United States Patent
Chu et al.

(10) Patent No.: US 7,516,934 B2
(45) Date of Patent: Apr. 14, 2009

(54) SAMPLE PLATE SUPPORT OF ADJUSTABLE ANGULAR ORIENTATION

(75) Inventors: Daniel Y. Chu, Hercules, CA (US); Paul J. Patt, Blackhawk, CA (US); Jeffry M. Ceremony, Fairfield, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 397 days.

(21) Appl. No.: 11/361,411

(22) Filed: Feb. 24, 2006

(65) Prior Publication Data

US 2007/0202018 A1    Aug. 30, 2007

(51) Int. Cl.
*F16M 13/00* (2006.01)

(52) U.S. Cl. .................. 248/550; 248/371; 422/104

(58) Field of Classification Search .............. 248/550, 248/349.1, 346.01, 637, 646, 652, 657, 660–662, 248/371, 396; 422/104

See application file for complete search history.

(56) References Cited

U.S. PATENT DOCUMENTS

| | | | | |
|---|---|---|---|---|
| 1,211,352 | A | * | 1/1917 | Rathburn .................... 248/657 |
| 4,433,824 | A | * | 2/1984 | Koosha ..................... 248/662 |
| 5,975,480 | A | * | 11/1999 | Schaefer et al. ............. 248/678 |
| 6,136,395 | A | | 10/2000 | Nova et al. |
| 6,450,782 | B1 | * | 9/2002 | Sakamoto .................. 417/359 |
| 6,722,395 | B2 | | 4/2004 | Overbeck et al. |
| 7,267,319 | B2 | * | 9/2007 | Vitrone ...................... 248/649 |

\* cited by examiner

*Primary Examiner*—Korie H. Chan
(74) *Attorney, Agent, or Firm*—Townsend and Townsend and Crew LLP; M. Henry Heines

(57) ABSTRACT

A platform that supports a sample plate such as a microtiter plate, a multi-well plate of any size, or a glass slide with sample spots distributed over its surface, and presents the plate for assay detection by a movable scanning head that has a field depth on the millimeter scale is leveled or otherwise adjusted in a planar orientation by an apparatus that includes a rocker plate, position sensors, and motorized risers arranged on the apparatus to provide the rocker plate with tilting capability along either or both or two orthogonal axes.

8 Claims, 4 Drawing Sheets

SAMPLE PLATE SUPPORT OF ADJUSTABLE ANGULAR ORIENTATION

BACKGROUND OF THE INVENTION

1. Field of the Invention

This invention resides in the field of laboratory equipment used in performing simultaneous assays on a multitude of species or reaction media in individual spots on a microscope slide or in individual wells of a microtiter plate or multi-well plates in general that are designed for performing large numbers of simultaneous small-volume assays. In particular, this invention addresses issues that arise when assays on these slides or plates are read or monitored by optical scanning.

2. Description of the Prior Art

Multi-well plates of many sizes, including the standard microtiter plate with 96 wells in a 12×8 array and a spacing of 9 mm between wells, as well as plates with as few as six or as many as several thousand wells, are widely used in biochemical laboratories. Large numbers of small samples are assayed simultaneously on these plates by automated instrumentation for purposes such as screening, determining binding affinities or other structural characteristics, or otherwise characterizing the samples. Glass slides with two-dimensional arrays of spots or microdots printed on their surfaces are used in an analogous fashion, the spots or microdots containing even smaller samples. The species analyzed on these wells and spots are often biological species such as proteins, peptide sequences, or nucleic acid fragments. Plates and slides of these types are also used for testing small molecule libraries synthesized by chemical laboratories and supplied to researchers for studies in cheminformatics and bioinformatics, where molecules in the libraries are screened for chemical or biological activity such as gene function and target binding.

Optical scanning is a highly effective means of detection for assays performed on these plates and slides, since optical scanner heads can rapidly traverse the entire array while focusing on individual wells or spots in succession and performing all of the functions of detection at each site. Optical data is also readily stored, quantified, and processed by automated instrumentation. To achieve high performance with large arrays of small wells or spots, the most effective optical scanning systems are those that have limited depth of field. Limited field depths and limited field detection systems are more effective in rejecting background fluorescence than are systems with a large field of view and depth of focus.

Optical scanning systems typically use confocal optics with a depth of field of about 1 to 10 microns. Accurate detection with such a short depth of field requires a high degree of uniformity of the spacing between each sample and the scanner head optical system.

To achieve close tolerance with such a short depth of field, many multi-well plates are constructed with flat bottoms of glass or other transparent material to allow scanning to be performed through the bottom of the plate. This is particularly effective when the solvents and other suspending media have been removed from the wells and the reaction species are deposited in a layer on the floor of each well. Even when scanning is performed through the bottom plate, however, the plate must be held in a level position with all areas of the bottom plate at the same distance from the travel plane of the scanning head to achieve accurate and uniform scanning. Minute defects in the plate such as variations in the thickness of the transparent bottom and warpage of the plate can cause this distance to vary from one site on the plate to the next and thereby interfere with the scanning accuracy. Similar variations occur in glass slides, where the thickness of the typical slide can vary by 50 microns or more.

SUMMARY OF THE INVENTION

These and other concerns and limitations are addressed by the present invention, which resides in a combination of a base plate and a sample plate support platform mounted to the base plate through two or more independent motorized risers whose heights are governed by position sensors that detect deviations between the support platform and a selected plane of reference. The plane of reference will be one that is parallel to the travel plane of the scanner head and at a distance that will allow the scanner head to properly focus on the sample sites. The risers are positioned to allow the support platform to tilt around axes in two orthogonal directions independently to correct for deviations in any direction. In view of this tilting capability, the support platform is also referred to herein as a rocker plate. The term "sample plate" is used herein for convenience to denote both well plates and slides with spots or microdots, and the support platform is constructed to support a sample plate by either allowing the sample plate to rest on the surface of the platform by the force of gravity alone or by securing the sample plate to the support platform in a manner that prevents the support plate from sliding laterally, or lifting above the support platform, or both. The support platform may itself be either a continuous plate or a grid or frame or any construction that will provide stable support for the sample plate, and the base plate may likewise be either a continuous plate, grid or frame or any construction that will provide for a controlled leveling or angling of the support platform. The terms "platform" and "plate" are thus used herein for convenience and are not restricted to solid slabs or even flat surfaces. By contrast, the sample site array on the sample plate, whether the sample plate is a multi-well plate or a slide with spots adhering to its surface, will be planar, as will be the path of travel of the scanner head. If necessary, the sample site array will be rendered planar by an auxiliary unit, as described below. With a planar sample array, adjustments to the orientation of the support platform and hence the sample plate by the motorized risers will be such as to render the plane of the sample sites parallel to the plane of the scanner head.

In preferred embodiments of this invention, the support platform contains a carriage that travels parallel to the base plate in one or more directions, or components such as rails along which a carriage can travel. The carriage can be an auxiliary unit to support the sample plate and hold the sample plate in a planar configuration, as mentioned in the preceding paragraph. The capability of movement parallel to the base plate is useful as a means of providing the scanner head with access to different regions on the sample plate. Thus, while the typical scanner head is designed to travel along an x-axis, for example, such as across the width of a single row of sample sites, the rails can supply a means for moving the sample plate along the y-axis to advance from one row to the next. The rate of travel and the position of the sample plate along the y-axis can be closely controlled by an appropriate motor, optionally with a position sensor. In further preferred embodiments of this invention, the scanner head is supported by the base plate, and thus the travel plane of the scanner head is established by the orientation of the base plate.

The auxiliary unit mentioned above, which is an optional addition to the apparatus of this invention, may provide any of various functions. A function of particular interest is the planar alignment of the sample sites on the sample plate. For sample plates that are multi-well plates, of which standard microtiter plates are one example, one such alignment device is a well registration device as described in co-pending, commonly owned Chu, D. Y., U.S. patent application Ser. No. 11/339,087, filed Jan. 24, 2006 (title: "Planar Registration of Multi-Well Plate from Well Side"), the contents of which are incorporated herein by reference. The device described in this document is one that urges the floors of all wells in an inverted multi-well plate into a common plane, i.e., the device flattens the plane of the well floors, and thereby corrects for any deviations that are present in the bottom surface of the plate. The apparatus of the present invention will serve a function complementary to that of the device of application Ser. No. 11/339,087 by maintaining the plane in a level orientation parallel to the travel plane of the scanner head.

Still further features, embodiments, objects, and advantages of the invention will be apparent from the description that follows.

DETAILED DESCRIPTION OF THE INVENTION AND PARTICULAR EMBODIMENTS

Figure 1:
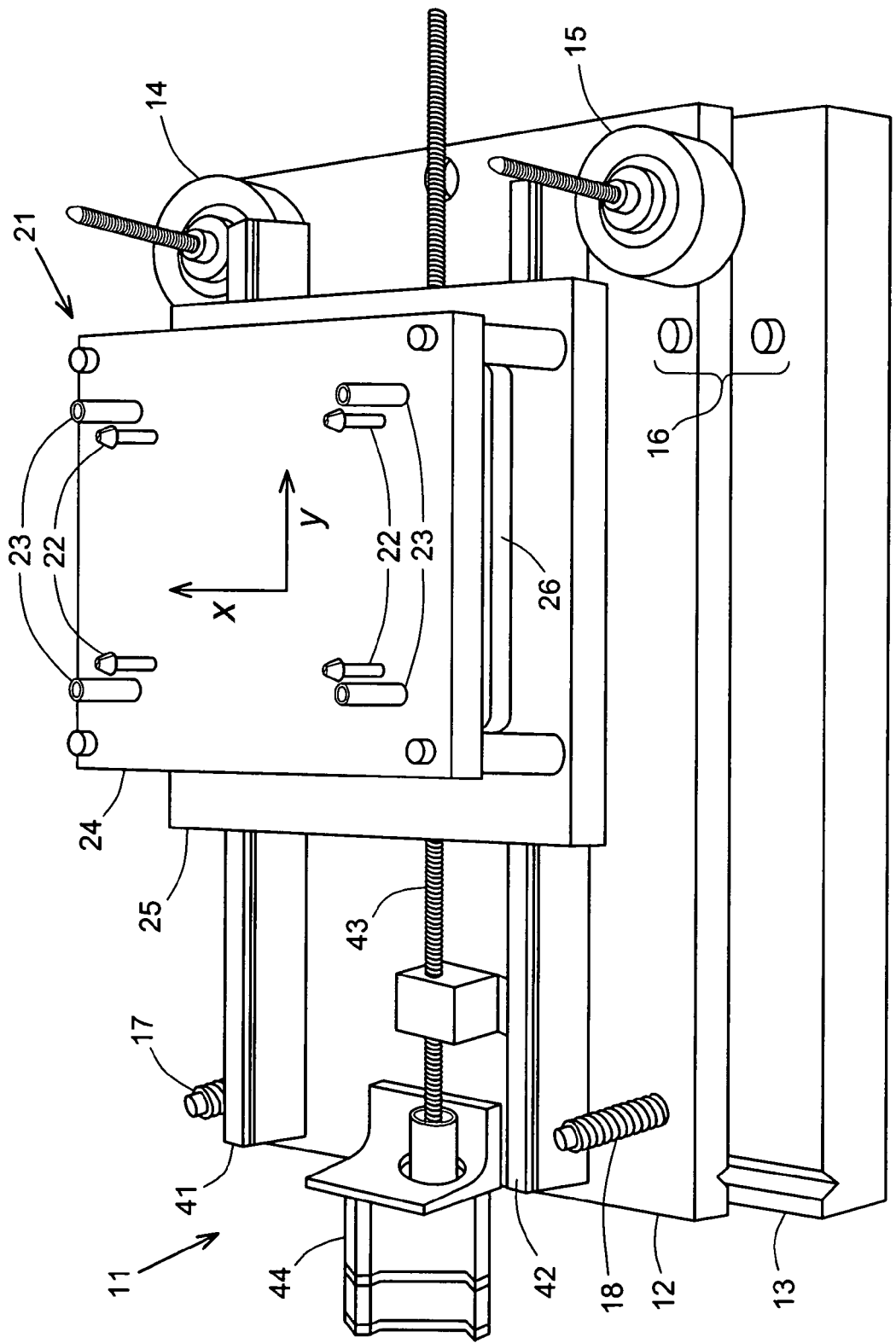
FIG. 1 is a perspective view of a unit in accordance with the present invention in combination with a microtiter plate flattening unit as depicted in co-pending application Ser. No. 11/339,087, referenced above.

While the features defining this invention are capable of implementation in a variety of constructions, the invention as a whole will be best understood by a detailed examination of a specific embodiment. One such embodiment is shown in the drawings.

FIG. 1 shows, in perspective, a unit 11 in accordance with the present invention that includes a support platform 12, which is referred to in this embodiment as a rocker plate, with a variable height and angular orientation. Components of the unit 11 include the rocker plate 12, a base plate 13, motorized risers 14, 15, position sensors (of which only one 16 is visible), and tension springs 17, 18. Also shown in the drawing is a microtiter plate flattening unit 21 in accordance with the disclosures in application Ser. No. 11/339,087, referenced above. As described in that application, the flattening unit 21 includes collets 22 that seize individual wells of an inverted microtiter plate and draw the seized wells downward until their floors abut the upper extremities of posts 23 extending above the collets, thereby forcing the well floors into planar registration to eliminate any warpage in the microtiter plate. As also described in application Ser. No. 11/339,087, the flattening unit includes an upper plate 24 and a lower plate 25, both fixed, and a movable inner plate 26 that controls the action of the collets 22.

Figure 2:
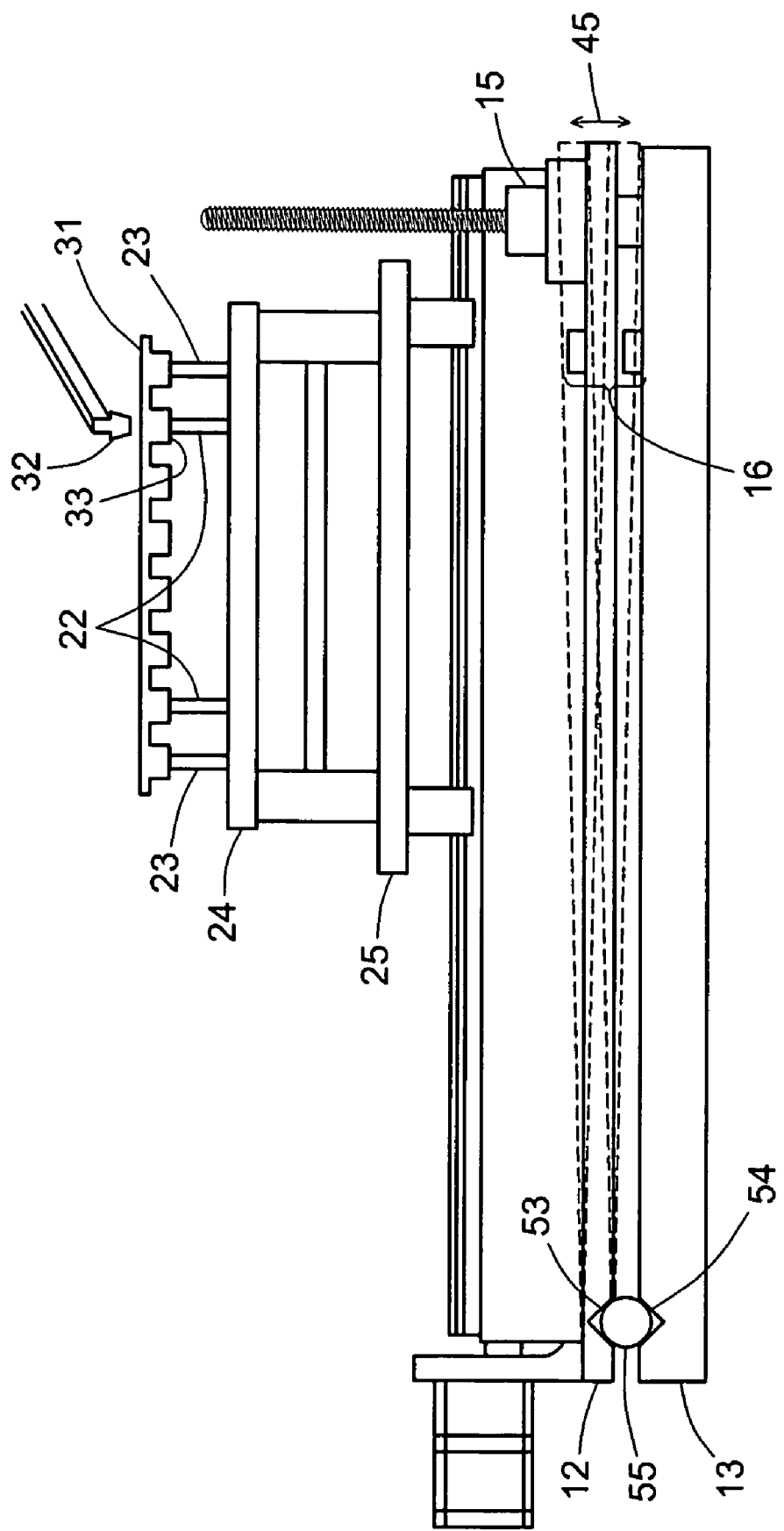
FIG. 2 is a side view of the units of FIG. 1 plus an inverted microtiter plate.

FIG. 2 is a side view of the components shown in FIG. 1, together with an inverted microtiter plate 31 and a scanner head 32. As disclosed in application Ser. No. 11/339,087, selected wells 33 of the microtiter plate, with their openings facing down, are seized by the collets 22 that draw the seized wells down until the adjacent wells abut the tips of the posts 23.

Returning to FIG. 1, two parallel rails 41, 42 are mounted to the upper surface of the rocker plate 12. The lower plate 25 of the microplate flattening unit 21 rests on these rails 41, 42 and the entire flattening unit 21 and the microtiter plate (shown only in FIG. 2) that is secured to the flattening unit by the collets 22 are movable along the rails in the direction of the y-axis. Such movement is achieved in this particular embodiment by a screw drive 43 driven by a conventional motor 44. Any conventional motor that can operate a screw drive can be used, preferably a motor that offers a high degree of precision. Stepper motors and dc motors are examples, as are motors that turn a spur pinion and drive a rack connected to the fixed plates of the flattening unit 21. Alternatives to the screw drive itself are belt drives and piezo drives. The scanner head 32 of FIG. 2 moves along the x-axis in a reciprocating motion, and by coordinating the travel of the scanner head 32 with the travel of the microtiter plate flattening unit 21, all wells in the full two-dimensional array in the microtiter plate are placed in the optical path of the scanner head and detection is performed on all samples. Systems and apparatus for moving the scanner head in this manner are disclosed in the following co-pending, commonly owned patent applications, both incorporated herein by reference in their entirety: Patt, P. J., et al., U.S. patent application Ser. No. 11/265,000, filed Nov. 1, 2005 (title: "Moving Coil Actuator for Reciprocating Motion with Controlled Force Distribution"); and Chu, D. Y., U.S. patent application Ser. No. 11/291,423, filed Nov. 30, 2005 (title: "Moving Coil Actuator with Expandable Range of Motion").

Figure 3:
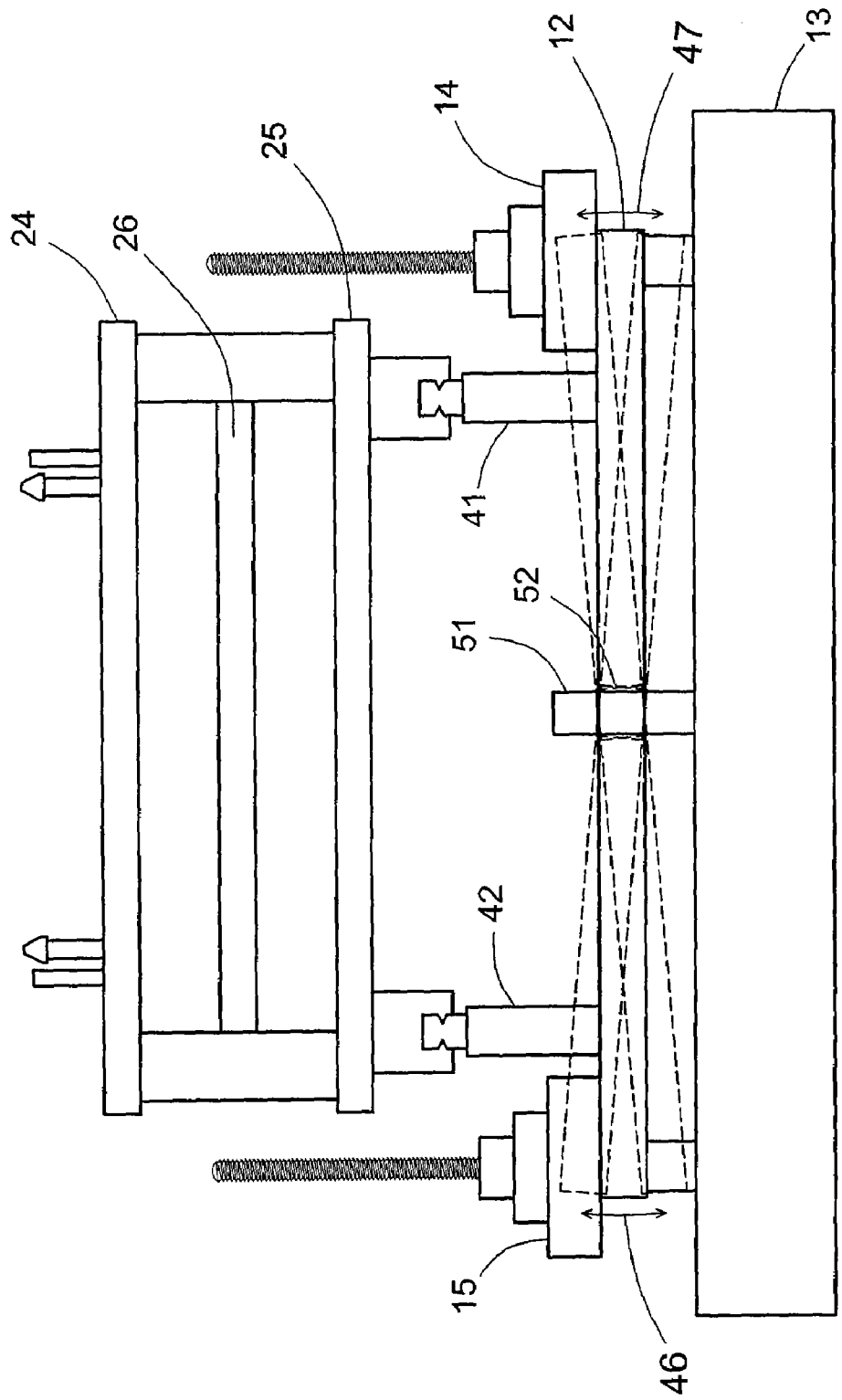
FIG. 3 is an end view of the units of FIG. 1.

FIG. 3 is an end view of the components of FIG. 1, taken from the end to the right according to the view shown in FIG. 1. The motorized risers 14, 15 are positioned at the two corners of the rectangular rocker plate 12 at this end of the plate. The risers join the rocker plate 12 to the base plate 13, and each riser independently establishes the distance between the rocker plate 12 and the base plate 13 at the location of the riser. Each riser can be any type of high-precision motor that can receive a signal, preferably an electronic signal, and respond to the signal by adjusting the height of the rocker plate 12. Examples of suitable motors are stepper motors and dc motors; other examples will be apparent to those skilled in the art. In this particular embodiment of the invention, the signal governing the action of these motors is generated by position sensors that are positioned to detect the height of the rocker plate at locations that are close to the two end corners shown in FIG. 3. In the configuration used in this embodiment, the position sensors are behind the risers in the view shown in FIG. 3 and therefore not visible in this Figure. As noted above, one of the sensors 16 is visible in FIG. 1. Two position sensors are thus used, one for each of the two corners and each sending an independent signal to the riser closest to it. With this independent action, the risers 14, 15 can tilt the end of the rocker plate 12 in the direction indicated by the arrows 46, 47 into the orientations shown by the dashed lines. In addition, and referring back to FIG. 2, the risers 14, 15 can lift or lower the entire end of the rocker plate as indicated by the arrow 45 and the dashed lines of FIG. 2. The rocker plate can thus be tilted along either or both of two orthogonal axes, one perpendicular to the plane of FIG. 2 and the other perpendicular to the plane of FIG. 3. The position sensors can be any of the variety of components that are known for this purpose, including displacement transducers operating by capacitive, inductive, photoconductive, or potentiometric detection, and Hall-effect sensors activated by magnets. Hall-effect sensors are presently preferred, an example of which is part no. A3240EUA available from Allegro MicroSystems, Inc. (Worcester, Mass., USA). As an alternative to the use of position sensors located on the rocker plate, the risers can be governed by a light intensity signal generated by the scanner head itself. The intensity of light collected by the scanner head will be greatest when the sample is at the focal length of the scanner head lens, and the system can be programmed to adjust the risers to achieve the maximum signal from each sample site.

Figure 4:
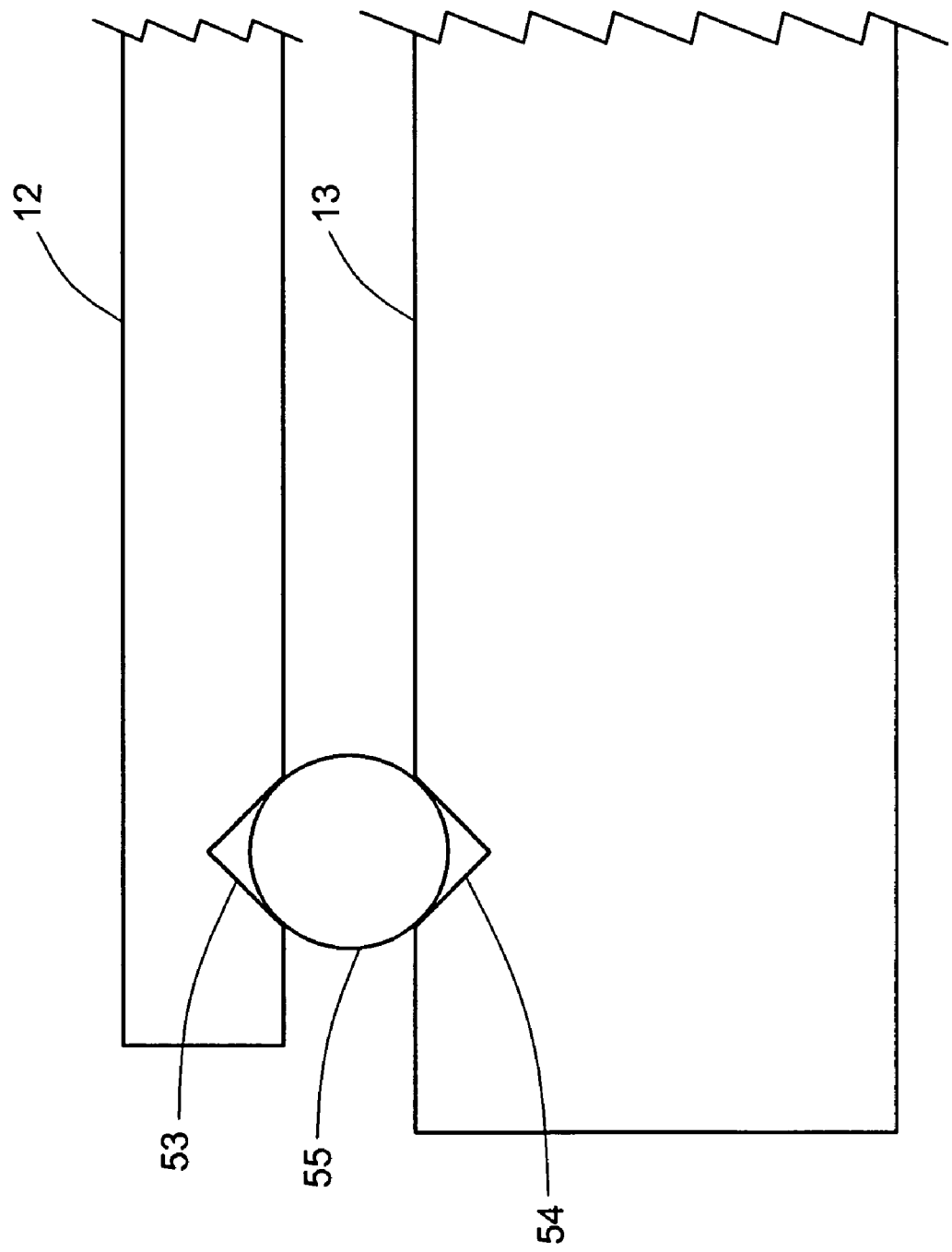
FIG. 4 is an enlargement of one end of the base and rocker plates of the unit of FIG. 1.

Stabilization of the rocker plate 12 in the embodiment shown while still permitting the angular variations described above is achieved by two components. One is a guide pin 51 (FIG. 3) secured to the base plate 13 and extending upward through an aperture 52 in the rocker plate. The guide pin 51 prevents the rocker plate from sliding laterally relative to the base plate along either the x-axis or the y-axis. The aperture 52 is conical in shape and wide enough to provide clearance around the guide pin 51 to accommodate the different angles of the rocker plate. The second stabilizing component, visible in FIGS. 2 and 4, is at the opposite end of the rocker plate and consists of grooves 53, 54 in opposing faces of the rocker plate 12 and base plate 13, respectively, and a roller 55 positioned within the grooves to allow the angle between the plates to vary while the roller remains within both grooves. The grooves are preferably V-shaped as shown, and the roller is of a shape that will allow the rocker plate to tilt along both orthogonal axes. Examples of such shapes are a sphere and an elongate member such as an ellipsoid.

Further control of the rocker plate 12 is provided by the tension springs 17, 18 (FIG. 1). Each of these springs surrounds a shaft (not visible in the Figure) that terminates in the base plate 13 while the spring itself resides above the rocker plate 12. Each spring is under compressive tension urging the end of the rocker plate that is opposite the end controlled by the motorized risers downward toward the base plate 13.

The apparatus of this invention can be used without an auxiliary unit 21 or a unit that performs an equivalent function, and the risers can be actuated and rocker plate adjusted at intervals throughout the course of a scan, such as a separate adjustment for each scan line. When the auxiliary unit 21 or its equivalent can be used, a single adjustment for the entire sample plate may suffice.

The foregoing description is offered primarily for purposes of illustration, and while the description describes various alternatives to the components shown in the Figures, still further alternatives that are still within the scope of the invention will be readily apparent to those skilled in the art.

What is claimed is:

1. Apparatus for supporting a sample plate and controlling the orientation of a plate so supported, said apparatus comprising:
    a base plate;
    a support platform having orthogonal axes and means for maintaining contact of said support platform with said base plate at one end of said support platform while allowing said support platform to tilt relative to said base plate along either or both of said orthogonal axes;
    means for detecting the angular orientation of said support platform relative to a selected plane and for generating a signal representative of said angular orientation; and
    first and second motorized risers joining said support platform to said base plate and positioned to tilt said support platform relative to said base plate independently along said orthogonal axes in response to said signal.

2. The apparatus of claim 1 wherein said means for detecting the angular orientation of said support platform are position sensors mounted to said support platform.

3. The apparatus of claim 1 wherein said means for detecting the angular orientation of said support platform is a scanner head above said support platform.

4. The apparatus of claim 1 wherein said means for maintaining contact of said support platform with said base plate are comprised of opposing grooves in said support platform and said base plate and a roller residing within said grooves.

5. The apparatus of claim 1 wherein said first and second motorized risers are stepper motors.

6. The apparatus of claim 1 further comprising means for preventing lateral movement of said support platform in directions parallel to said base plate.

7. The apparatus of claim 1 wherein said means for maintaining contact of said support platform with said base plate are located at a first end of said support platform and said apparatus further comprises biasing means for biasing a second end of said support platform away from said base plate, said second end opposite said first end.

8. The apparatus of claim 1 wherein said biasing means are spring means applying compressive tension between said support platform and said base plate.

* * * * *